United States Patent [19]

Eistetter et al.

[11] 4,395,414
[45] Jul. 26, 1983

[54] SUBSTITUTED QUINOLINONE-ALKANECARBOXYLIC ACIDS AND MEDICAMENTS CONTAINING THEM, HAVING A HYPERGLYCAEMIC ACTION

[75] Inventors: Klaus Eistetter, Constance; Erich Rapp, Radolfzell; Horst Wolf, Constance, all of Fed. Rep. of Germany

[73] Assignee: Byk Gulden Lomberg Chemische Fabrik Gesellschaft mit Beschränkter Haftung, Constance, Fed. Rep. of Germany

[21] Appl. No.: 256,247

[22] Filed: Apr. 21, 1981

[30] Foreign Application Priority Data

Aug. 14, 1980 [EP] European Pat. Off. ........ 80104800.0

[51] Int. Cl.³ .................... A61K 31/47; C07D 215/22
[52] U.S. Cl. ..................................... 424/258; 546/157
[58] Field of Search ................... 546/157; 424/258

[56] References Cited

U.S. PATENT DOCUMENTS 3,994,900 11/1976 Krapcho et al. ............... 424/258 X
4,006,148 2/1977 Wehrmeister ..................... 546/157
4,232,027 11/1980 Turk et al. ........................ 424/258

FOREIGN PATENT DOCUMENTS 24638 3/1981 European Pat. Off. .

OTHER PUBLICATIONS

Eistetter, et al., Chemical Abstracts, vol. 95, 80,757b, (1981).
Surrey, J. AM. Chem. Soc., vol. 70, pp. 2190-2193, (1948).
Gyul'budagyan, et al., Chemical Abstracts, vol. 93, 204425x, (1980).

Primary Examiner—Donald G. Daus
Assistant Examiner—Diana G. Rivers
Attorney, Agent, or Firm—Berman, Aisenberg & Platt

[57] ABSTRACT

Quinolinone-alkanecarboxylic acids of the formula I

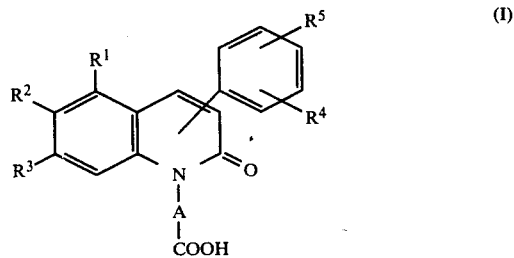

wherein
$R^1$, $R^2$ and $R^3$ are identical or different and denote a hydrogen atom, a halogen atom, a hydroxyl group, an alkoxy group with 1 to 4 carbon atoms, an amino group, a dialkylamino group, the alkyl radicals having 1 to 4 carbon atoms, or a nitro group,
$R^4$ and $R^5$ are identical or different and denote a hydrogen atom, a halogen atom, an alkoxy group with 1 to 4 carbon atoms, a hydroxyl group, an amino group or a dialkylamino group, the alkyl radicals having 1 to 4 carbon atoms, or
$R^4$ and $R^5$ together denote a methylenedioxy group bonded to two adjacent ring carbon atoms, and A denotes an alkylene group with 1 to 5 carbon atoms,
and esters thereof with alkanols with 1 to 5 carbon atoms, and salts thereof with inorganic and organic bases are new compounds. They display a hyperglycaemic action in warm-blooded animals. Processes for the preparation of the new compounds are given.

8 Claims, No Drawings

SUBSTITUTED QUINOLINONE-ALKANECARBOXYLIC ACIDS AND MEDICAMENTS CONTAINING THEM, HAVING A HYPERGLYCAEMIC ACTION

The invention relates to substituted quinolinone-alkanecarboxylic acids, their preparation and use, and medicaments containing them.

The invention relates to new substituted quinolinones of the general formula I

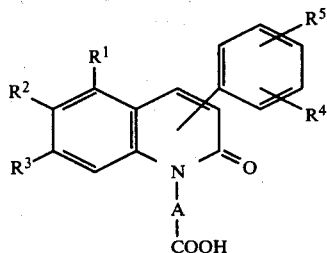

wherein
$R^1$, $R^2$ and $R^3$ are identical or different and denote a hydrogen atom, a halogen atom, a hydroxyl group, an alkoxy group with 1 to 4 carbon atoms, an amino group, a dialkylamino group, the alkyl radicals having 1 to 4 carbon atoms, or a nitro group,
$R^4$ and $R^5$ are identical or different and denote a hydrogen atom, a halogen atom, an alkoxy group with 1 to 4 carbon atoms, a hydroxyl group, an amino group or a dialkylamino group, the alkyl radicals having 1 to 4 carbon atoms, or
$R^4$ and $R^5$ together denote a methylenedioxy group bonded to two adjacent ring carbon atoms, and A denotes an alkylene group with 1 to 5 carbon atoms, and esters thereof with alkanols with 1 to 5 carbon atoms, and salts thereof with inorganic and organic bases.

An alkoxy group with 1 to 4 carbon atoms can be the methoxy, ethoxy, 1- or 2-propoxy, 1- or 2-n-butoxy, isobutoxy, sec.-butoxy or tert.-butoxy group.

Examples which may be mentioned of an alkyl radical with 1 to 4 carbon atoms in a dialkylamino group are the methyl, ethyl, propyl, isopropyl, n-butyl, isobutyl and sec.-butyl radical, unbranched alkyl radicals being preferred. The dimethylamino group and the diethylamino group are particularly preferred as the dialkylamino group.

An alkylene group with 1 to 5 carbon atoms can be, for example, a methylene, ethylene, ethylidene, trimethylene, propylene, propylidene, isopropylidene, tetramethylene, 1,2-dimethylethylene, 1,1-dimethylethylene, 1-butylidene, 2-butylidene, isobutylidene, ethylethylene, 1-methylpropylene, pentamethylene, 2-methyltetramethylene or 2,2-dimethyltrimethylene group. Those alkylene groups A which, in the general formula I, have a methylene group in the vicinity of the nitrogen atom, that is to say do not carry a side chain in the vicinity of the nitrogen atom, are preferred. The methylene, ethylene, propylene, tetramethylene and pentamethylene group are particularly preferred.

Examples of possible alkanols with 1 to 5 carbon atoms are methanol, ethanol, propanol, isopropanol, n-butan-1-ol, n-butan-2-ol, isobutanol, tert.-butanol, n-pentan-1-ol, -2-ol or -3-ol, 3-methylbutan-1-ol or -2-ol, 3-methylbutan-1-ol or -2-ol and 2,2-dimethylpropanol.

Fluorine, chlorine, bromide and iodine are understood as halogen atoms, chlorine and bromine, and especially chlorine, being preferred.

Possible salts are salts with inorganic and organic bases. Salts which are not pharmacologically acceptable are converted, by methods which are known per se, into pharmacologically acceptable salts, which are the preferred salts according to the invention. Cations which are used for the salt formation are, above all, the cations of alkali metals, alkaline earth metals or earth metals. However, the corresponding cations of organic nitrogen bases, such as amines, aminoalkanols, aminosugars, basic aminoacids can also be used.

The salts of lithium, sodium, potassium, magnesium, calcium, aluminium, ethylenediamine, dimethylamine, diethylamine, morpholine, piperidine, piperazine, N-lower alkylpiperazine (for example N-methylpiperazine), methylcyclohexylamine, benzylamine, ethanolamine, diethanolamine, triethanolamine, tris-(hydroxymethyl)-aminomethane, 2-amino-2-methylpropanol, 2-amino-2-methyl-1,3-propanediol, glucamine, N-methylglucamine, glucosamine, N-methylglucosamine, lysine, ornithine, arginine and quinoline, may be mentioned as examples.

Substituted quinolinones of the general formula I*

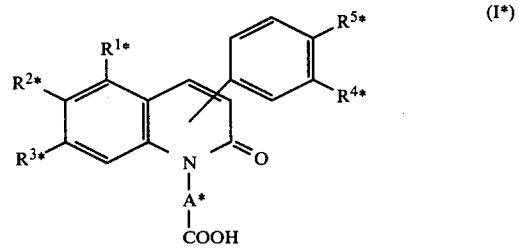

wherein
$R^{1*}$, $R^{2*}$ and $R^{3*}$ are identical or different and denote a hydrogen atom, a halogen atom, an alkoxy group with 1 to 4 carbon atoms or a hydroxyl group,
$R^{4*}$ and $R^{5*}$ are identical or different and denote a hydrogen atom, a halogen atom, an alkoxy group with 1 to 4 carbon atoms or a hydroxyl group, or
$R^{4*}$ and $R^{5*}$ together denote a methylenedioxy group, and
$A^*$ denotes an alkylene group with 1 to 5 carbon atoms, and esters thereof with alkanols with 1 to 5 carbon atoms, and salts thereof with inorganic and organic bases, are preferred.

Substituted quinolinones of the general formula I**

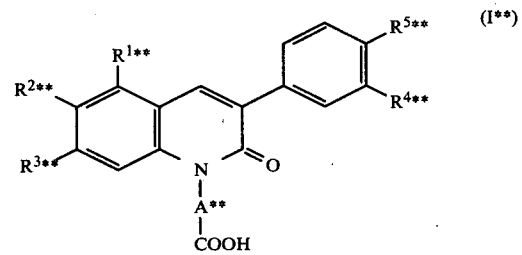

wherein
$R^{1}$ and $R^{2}$ denote a hydrogen atom,

R³** denotes a hydrogen atom or a chlorine atom,
R⁴ and R⁵ are identical or different and denote a hydrogen atom, a chlorine atom or a methoxy group and
A** denotes a methylene, ethylene, n-propylene or n-butylene group,
and methyl and ethyl esters thereof and salts thereof with inorganic and organic bases, are particularly preferred.

Examples of compounds according to the invention which may be mentioned are: 3-(2-bromo-3,4-methylenedioxyphenyl)-1,2-dihydro-2-oxoquinol-1-yl-acetic acid, 4-[1,2-dihydro-3-(4-nitrophenyl)-2-oxoquinol-1-yl]-butyric acid ethyl ester, 2-(7-amino-1,2-dihydro-6-methyl-2-oxo-3-phenyl-quinol-1-yl)-propionic acid, 3-(7-amino-1,2-dihydro-6-methyl-2-oxo-3-phenyl-quinol-1-yl)-propionic acid, 1,2-dihydro-6,7-dimethoxy-2-oxo-3-phenyl-quinol-1-yl-acetic acid, 4-[7-amino-3-(4-chlorophenyl)-1,2-dihydro-2-oxo-quinol-1-yl]-butyric acid ethyl ester, 5-[1,2-dihydro-7-methoxy-3-(3,4-dimethoxyphenyl)-2-oxo-quinol-1-yl]-valeric acid, 1,2-dihydro-5-nitro-3-(4-nitrophenyl)-2-oxo-quinol-1-yl-acetic acid isopropyl ester, 4-[1,2-dihydro-6-methoxy-3-(3,4-methylenedioxyphenyl)-2-oxo-quinol-1-yl]-butyric acid, 3-[3-(4-bromophenyl)-1,2-dihydro-6-methoxy-2-oxo-quinol-1yl]-propionic acid methyl ester, 3-[3-(4-ethoxyphenyl)-1,2-dihydro-5-hydroxy-2-oxo-quinol-1-yl]-propionic acid, 2-[6-bromo-1,2-dihydro-3-(4-hydroxyphenyl)-2-oxo-quinol-1-yl]-isovaleric acid ethyl ester, 1,2-dihydro-6,7-dimethoxy-3-(3,4-methylenedioxyphenyl)-2-oxo-quinol-1-yl-acetic acid, 4-[3-(4-chlorophenyl)-1,2-dihydro-2-oxo-3-quinol-1-yl]-butyric acid, 3-(7-chloro-1,2-dihydro-1-oxo-3-phenyl-quinol-1-yl)-propionic acid, 3-(1,2-dihydro-2-oxo-4-phenyl-quinol-1-yl)-propionic acid, 6-(1,2-dihydro-2-oxo-4-phenyl-quinol1-yl)-caproic acid, 3-(7-chloro-1,2-dihydro-2-oxo-3-phenyl-quinol-1-yl)-propionic acid, 4-[1,2-dihydro-4-(3-nitrophenyl)-2-oxo-quinol-1-yl]-butyric acid methyl ester, 2-[1,2-dihydro-7-ethoxy-4-(4-hydroxyphenyl)-2-oxo-quinol-1-yl]-hexanoic acid ethyl ester, 7-chloro-3-(4-chlorophenyl)-1,2-dihydro-2-oxo-quinol-1-yl-acetic acid ethyl ester, 2-[1,2-dihydro-4-(4-hydroxyphenyl)-2-oxo-quinol-1-yl]-propionic acid, 2-[1,2-dihydro-7-methoxy-4-(3,4-dimethoxyphenyl)-2-oxo-quinol-1-yl]-butyric acid, 3-(1,2-dihydro-2-oxo-4-phenyl-quinol-1-yl)-propionic acid and 4-(1,2-dihydro-2-oxo-4-phenyl-quinol-1-yl)-butyric acid.

Preferred compounds according to the invention, which are distinguished by interesting actions, are: 7-chloro-1,2-dihydro-2-oxo-3-phenyl-quinol-1-yl-acetic acid, 1,2-dihydro-2-oxo-3-phenyl-quinol-1-yl-acetic acid, 3-(7-chloro-1,2-dihydro-2-oxo-3-phenyl-quinol-1-yl)-propionic acid, 4-[1,2-dihydro-3-(4-methoxyphenyl)-2-oxo-quinol-1-yl]-butyric acid and 4-[3-(4-chlorophenyl)-1,2-dihydro-2-oxo-quinol-1-yl]-butyric acid, their pharmacologically acceptable salts and their esters with alkanols with 1 to 4, preferably 1 or 2, carbon atoms.

The compounds according to the invention have valuable pharmacological properties which render them commercially useful. They have a hyperglycaemic action and activate the formation of glucose in the liver.

Because of their advantageous activity, the quinolinone-alkanecarboxylic acids according to the invention and their esters and salts are suitable for the treatment or prophylaxis of illnesses based on disorders in glucose metabolism. For example, conditions which are based on insufficient synthesis of glucose in the liver and which are clinically associated with hypoglycaemia and/or ketonaemia are treated. Examples which may be mentioned of such conditions in need of treatment are postnatal hypoglycaemia in new-born babies, hypoglycaemia caused by abuse of alcohol, and physical states of exhaustion after strenuous physical exertion or prolonged fasting, or hyperinsulinism. The compounds according to the invention are also suitable for normalising an increased level of lactate in the blood and body tissue regardless of the origin. The illnesses mentioned occur not only in humans but to the same extent in mammals, in particular useful animals. The compounds according to the invention and medicaments containing these compounds are thus suitable, for example, for the prophylaxis and therapy of hypoglycaemia in suckling piglets. Ruminants, in particular cattle reared for a high milk output, are particularly affected by such illnesses based on disorders in glucose metabolism. The compounds according to the invention are particularly suitable for the prophylaxis and therapy of widespread ketosis in ruminants, especially in dairy cows. Both the primary and the secondary and subclinical form of ketosis can be treated with the compounds according to the invention.

It was hitherto only possible to stimulate gluconeogenesis with the aid of hormones, such as glucagon, adrenocorticotropic hormone (ACTH) and glucocorticoids. However, a hormone treatment of this type also produces undesired side effects, such as, for example, catabolism and increased risk of infection.

The invention thus also relates to a method for combating the illnesses mentioned by administration of the compounds according to the invention. The invention furthermore relates to the use of the compounds according to the invention in combating the illnesses mentioned. The invention also relates to the use of the compounds according to the invention for the preparation of medicaments for combating the illnesses mentioned.

The invention furthermore relates to medicaments which contain one or more of the substituted quinolinones of the general formula I

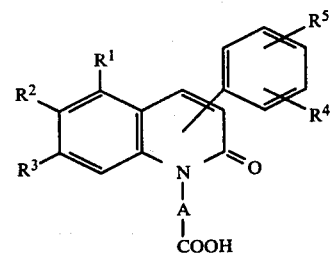

(I)

wherein
R¹, R² and R³ are identical or different and denote a hydrogen atom, a halogen atom, a hydroxyl group, an alkoxy group with 1 to 4 carbon atoms, an amino group, a dialkylamino group, the alkyl radicals having 1 to 4 carbon atoms, or a nitro group,
R⁴ and R⁵ are identical or different and denote a hydrogen atom, a halogen atom, an alkoxy group with 1 to 4 carbon atoms, a hydroxy group, an amino group or a dialkylamino group, the alkyl radicals having 1 to 4 carbon atoms, or
R⁴ and R⁵ together denote a methylenedioxy group bonded to two adjacent ring carbon atoms, and A denotes an alkylene group with 1 to 5 carbon atoms,
and/or esters thereof with alkanols with 1 to 5 carbon atoms, and/or pharmacologically acceptable salts thereof with inorganic or organic bases.

Embodiments of the medicaments are those which contain substituted quinolinones of the formulae I* and I** and/or alkyl esters thereof and/or pharmacologically acceptable salts thereof with inorganic or organic bases.

The medicaments are prepared by processes which are known per se. As medicaments, the new compounds can be employed as such or, if appropriate, in combination with suitable pharmaceutical excipients. If the new pharmaceutical formulations contain pharmaceutical excipients in addition to the active compounds, the content of active compound in these mixtures is 1 to 95, preferably 15 to 85, percent by weight of the total mixture.

In accordance with the invention, the active compounds can be used, in the field of human medicine and in the field of veterinary medicine, in any desired form, for example systemically, provided that the establishment and maintenance of sufficient levels of active compounds in the blood or tissue are ensured. This can be achieved, for example, by oral or parenteral administration in suitable doses. The pharmaceutical formulation of the active compound is advantageously in the form of unit doses appropriate for the desired administration. A unit dose can be, for example, a tablet, a dragee, a capsule, a suppository or a measured volume of a powder, of a granular material, of a solution, of an emulsion or of a suspension.

"Unit dose" for the purpose of the present invention means a physically determined unit which contains an individual amount of the active ingredient in combination with a pharmaceutical excipient, the content of active compound in the unit dose corresponding to a fraction or multiple of a therapeutic individual dose. An individual dose preferably contains the amount of active compound which is given in one administration and usually corresponds to a whole daily dose or a half, one-third or one-quarter of the daily dose. If only a fraction, such as a half or one-quarter, of the unit dose is required for an individual therapeutic administration, the unit dose is advantageously divisible, for example in the form of a tablet with a breaking groove.

When in the form of unit doses and intended, for example, for administration to humans, the pharmaceutical formulations according to the invention contain 10 to 1,000 mg, advantageously 50 to 500 mg and in particular 100 to 300 mg, of active compound. Formulations according to the invention for use in the field of veterinary medicine contain amounts of active compound which are appropriately matched to the body weight and the metabolism of the animal. For administration to dairy cows, for example, formulations in unit doses which amount to 8 to 12 times the abovementioned amounts for human medicine have proved expedient. In general, it has proved advantageous in human medicine to administer the active compound or compounds, when these are given orally, in a daily dose of 0.3 to 150, preferably 1.5 to 75 and in particular 3 to 15 mg/kg of body weight, if appropriate in the form of several, preferably 1 to 3, individual administrations to achieve the desired results. An individual administration contains the active compound or compounds in amounts of 0.1 to 50, preferably 0.5 to 25 and in particular 1 to 5, mg/kg of body weight.

Similar dosages can be used in the case of parenteral treatment, for example intravenous or intramuscular administration. In this form of therapy, about 1 to 5 mg of active compound/kg of body weight are administered.

The daily dose for use in veterinary medicine is as a rule within the ranges indicated for human medicine. The expert is able to match the daily dose to the peculiarities of the animal to be treated.

In the case of long-term medication, the pharmaceutical formulation is in general administered, for therapeutic purposes, at fixed points in time, such as 1 to 4 times daily, for example after each meal or after the feed and/or in the evening. In acute cases, medication takes place at varying points in time. Under certain circumstances, it may be necessary to deviate from the dosages mentioned, and in particular to do so in accordance with the nature, the body weight and the age of the individual to be treated, the nature and the severity of the illness, the nature of the formulation and of the administration of the medicament and the period or interval within which administration takes place. Thus, in some cases, it may be sufficient to manage with less than the abovementioned amount of active compound, whilst in other cases the abovementioned amount of active compound must be exceeded. The optimum dosage and method of administration of the active compounds required in each particular case is determined by the expert on the basis of his expert knowledge.

The pharmaceutical formulations as a rule consist of the active compounds according to the invention and non-toxic, pharmaceutically acceptable medicinal excipients, which are used as an admixture or diluent in a solid, semi-solid or liquid form, or as a means of encasing, for example in the form of a capsule, a tablet coating, a sachet or some other container for the therapeutically active ingredient. An excipient can, for example, serve as a promoter for the absorption of the medicament by the body, as a formulating auxiliary, as a sweetener, as a flavour correctant, as a colourant or as a preservative.

Examples of forms which may be used orally are tablets, dragees, hard and soft capsules, for example made of gelatin, dispersible powders, granules, aqueous and oily suspensions, emulsions, solutions or syrups.

Tablets may contain inert diluents, for example calcium carbonate, calcium phosphate, sodium phosphate or xylitol; granulating agents and dispersing agents, for example calcium phosphate or alginates; binders, for example starch, gelatin or gum acacia; and lubricants, for example aluminium stearate or magnesium stearate, talc or silicone oil. The tablets may additionally be provided with a coating, which can also be such that delayed dissolution and resorption of the medicament in the gastro-intestinal tract and hence, for example, better toleration, a protracted effect or a retarded effect are achieved. Gelatin capsules may contain the medicament mixed with a solid diluent, for example calcium carbonate or kaolin, or an oily diluent, for example paraffin oil.

Aqueous suspensions may contain suspending agents, for example sodium carboxymethylcellulose, methylcellulose, hydroxypropylcellulose, sodium alginate, polyvinylpyrrolidone, gum tragacanth or gum acacia; dispersing agents and wetting agents, for example polyoxyethylene stearate, heptadecaethyleneoxycetanol, polyoxyethylene sorbitol monooleate, polyoxyethylene sorbitan monooleate or lecithin; preservatives, for example methyl hydroxybenzoate or propyl hydroxybenzoate; flavouring agents; and sweeteners, for example saccharin or sodium cyclamate.

Oily suspensions may contain, for example, paraffin oil and thickeners, such as beeswax, hard paraffin or cetyl alcohol; and furthermore sweeteners, flavouring agents and antioxidants.

Water-dispersible powders and granules may contain the medicaments mixed with dispersing agents, wetting agents and suspending agents, for example those mentioned above, as well as with sweeteners, flavouring agents and colourants.

Emulsions may contain, for example, paraffin oil, in addition to emulsifying agents, such as gum acacia, gum tragacanth, phosphatides, sorbitan monooleate or polyoxyethylene sorbitan monooleate, and sweeteners and flavouring agents.

Sterile injectable aqueous solutions, isotonic salt solutions or other solutions, which may contain dispersing agents or wetting agents and/or pharmacologically acceptable diluents, for example propylene glycol or butylene glycol, are used for parenteral administration of the medicaments.

The active compound or compounds can also be formulated in a micro-encapsulated form, if appropriate together with one or more of the excipients or additives mentioned.

If the compounds according to the invention are administered as a component of the animal feed or as a solution or suspension in the drinking water of the animal, it is expedient to disperse the compounds intimately in an inert carrier or diluent. By an inert carrier in this context there is understood a carrier which does not react with the compounds according to the invention and can be administered to the animals without danger. A substance which is or can be a constituent of the animal feed is preferably used as the carrier. Suitable carriers or diluents include customary feed additives, in which the compounds according to the invention are present in relatively large proportions and which are added to the feed directly or after a dilution or mixing operation. Such compositions can also be added to the animal feed. Typical carriers and diluents include dried cereal residues from distillers, maize flour, citrus flour, fermentation residues, ground oyster shells, maize cob flour, bean flour residues and soya grit. The compounds according to the invention are dispersed thoroughly in the carrier or diluent in the customary manner, by grinding, stirring, shaking or similar measures. Compositions which contain from 0.1 to 50 percent by weight, in particular from 0.5 to 25 percent by weight, of the compounds according to the invention are particularly suitable as feed additives. These additives are added to the animal feed in amounts such that the finished feed contains the amount of compounds according to the invention which has already been indicated above as necessary for prophylaxis and treatment.

In order to intensify the action of the compounds according to the invention, it is expedient simultaneously to add substrates for gluconeogenesis by the oral or peroral route. Examples of such substrates which can be used are lactic acid, propionic acid, aminoacids, glycerol and fats. The advantageous action of the compounds according to the invention can also be assisted by administration of energy carriers which can easily be utilised, such as, for example, glucose and other carbohydrates.

The invention furthermore relates to a process for the preparation of the substituted quinolinones of the general formula I

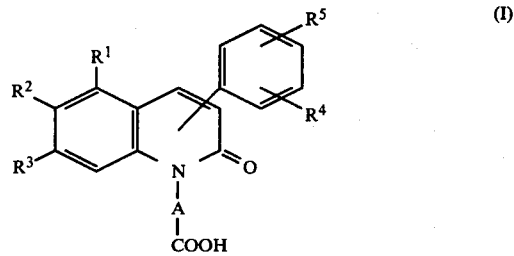

wherein
$R^1$, $R^2$ and $R^3$ are identical or different and denote a hydrogen atom, a halogen atom, a hydroxyl group, an alkoxy group with 1 to 4 carbon atoms, an amino group, a dialkylamino group, the alkyl radicals having 1 to 4 carbon atoms, or a nitro group,
$R^4$ and $R^5$ are identical or different and denote a hydrogen atom, a halogen atom, an alkoxy group with 1 to 4 carbon atoms, a hydroxyl group, an amino group or a dialkylamino group, the alkyl radicals having 1 to 4 carbon atoms, or
$R^4$ and $R^5$ together denote a methylenedioxy group bonded to two adjacent ring carbon atoms, and A denotes an alkylene group with 1 to 5 carbon atoms, and esters thereof with alkanols with 1 to 5 carbon atoms, and salts thereof with inorganic and organic bases, characterised in that a compound of the general formula II

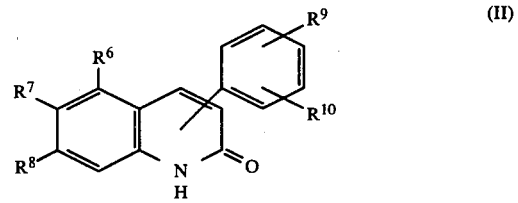

wherein
$R^6$, $R^7$, $R^8$, $R^9$ and $R^{10}$ denote a hydrogen atom, a halogen atom, an alkoxy group with 1 to 4 carbon atoms, a dialkylamino group, the alkyl radicals having 1 to 4 carbon atoms, or a nitro group, or
$R^9$ and $R^{10}$ together denote a methylenedioxy group bonded to two adjacent ring carbon atoms,
is reacted with a ω-halogenocarboxylic acid derivative of the general formula III

wherein
$R^{11}$ denotes a chlorine, bromine or iodine atom,
$R^{12}$ denotes a nitrile group, a carboxyl group or a carbalkoxy group, wherein an alkoxy radical contains 1 to 5 carbon atoms, and
A has the abovementioned meaning,
in the presence of a strong base, and, if appropriate, a radical $R^{12}$ which denotes a nitrile group is converted into a carboxyl group and, if desired, the radicals $R^6$, $R^7$, $R^8$, $R^9$ and $R^{10}$, if they denote nitro groups, are converted into amino groups, which, if desired, are converted into dialkylamino groups, and/or, if desired, the radicals $R^6$, $R^7$, $R^8$, $R^9$ and $R^{10}$, if they denote alkoxy groups, are converted into hydroxyl groups, an acid obtained is converted into a salt or an ester with a $C_1-C_5$-alkanol, a salt obtained is converted into the free acid, an ester with a $C_1$ to $C_5$-alkanol or another salt, or an ester obtained is converted into the free acid or into a salt or another ester.

The invention also relates to a process for the preparation of the substituted quinolinones of the general formula I*

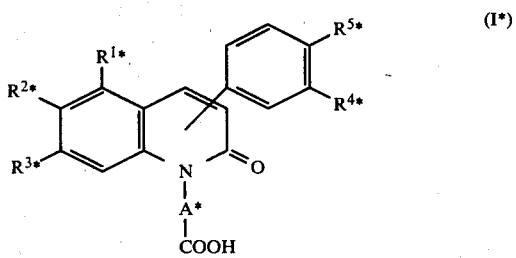

wherein
$R^{1*}$, $R^{2*}$ and $R^{3*}$ are identical or different and denote a hydrogen atom, a halogen atom, an alkoxy group with 1 to 4 carbon atoms or a hydroxyl group,
$R^{4*}$ and $R^{5*}$ are identical or different and denote a hydrogen atom, a halogen atom, an alkoxy group with 1 to 4 carbon atoms or a hydroxyl group, or
$R^{4*}$ and $R^{5*}$ together denote a methylenedioxy group, and
A* denotes an alkylene group with 1 to 5 carbon atoms,
and esters thereof with alkanols with 1 to 5 carbon atoms, and salts thereof with inorganic and organic bases, characterised in that a compound of the general formula II*

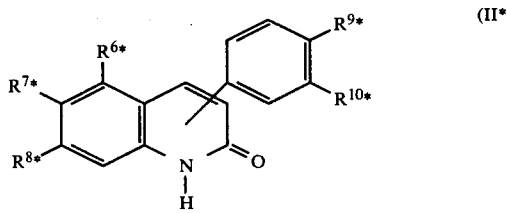

wherein
$R^{6*}$, $R^{7*}$, $R^{8*}$, $R^{9*}$ and $R^{10*}$ are identical or different and denote a hydrogen atom, a halogen atom or an alkoxy group with 1 to 4 carbon atoms, or
$R^{9*}$ and $R^{10*}$ together denote a methylenedioxy group,
is reacted with a ω-halogenocarboxylic acid derivative of the general formula III*

wherein
$R^{11*}$ denotes a chlorine or bromine atom,
$R^{12*}$ denotes a nitrile group, a carboxyl group or a carbalkoxy group, wherein an alkoxy radical has 1 to 5 carbon atoms, and
A* has the abovementioned meaning,
in the presence of a strong base and, if appropriate, a radical $R^{12*}$ which denotes a nitrile group is converted into a carboxyl group and, if desired, the radicals $R^{6*}$, $R^{7*}$, $R^{8*}$, $R^{9*}$ and $R^{10*}$, if they denote alkoxy groups, are converted into hydroxyl groups, an acid obtained is converted into a salt or an ester with a $C_1$ to $C_5$-alkanol, a salt obtained is converted into the free acid, an ester with a $C_1$ to $C_5$-alkanol or another salt, or an ester obtained is converted into the free acid or into a salt or another ester.

The invention also relates to a process for the preparation of the substituted quinolinones of the general formula I**

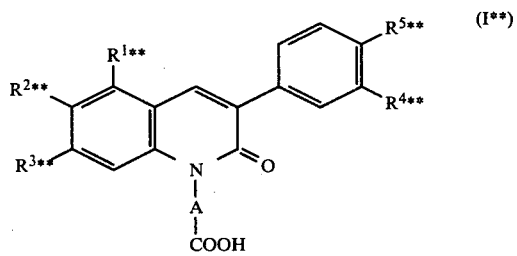

wherein
$R^{1}$ and $R^{2}$ denote a hydrogen atom,
$R^{3**}$ denotes a hydrogen atom or a chlorine atom,
$R^{4}$ and $R^{5}$ are identical or different and denote a hydrogen atom, a chlorine atom or a methoxy group and
A** denotes a methylene, ethylene, n-propylene or n-butylene group,
and methyl and ethyl esters thereof and salts thereof with inorganic and organic bases, characterised in that a compound of the general formula II**

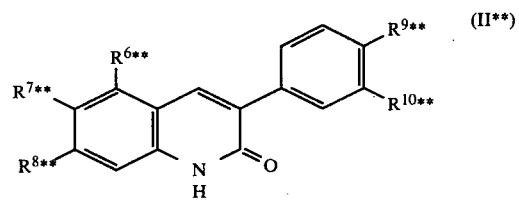

wherein
$R^{6}$ and $R^{7}$ denote a hydrogen atom,
$R^{8**}$ denotes a hydrogen atom or a chlorine atom and
$R^{9}$ and $R^{10}$ are identical or different and denote a hydrogen atom, a chlorine atom or a methoxy group,
is reacted with a ω-halogenocarboxylic acid derivative of the general formula III**

wherein
$R^{11**}$ denotes a bromine atom,
$R^{12**}$ denotes a carboxymethyl or carboxyethyl group and
A** has the abovementioned meaning,
in the presence of a strong base and, if desired, a methyl or ethyl ester obtained is converted into the free acid or into a salt, or a methyl ester is converted into the ethyl ester.

An embodiment of the process according to the invention for the preparation of the compounds of the general formulae I, I* and I** wherein $R^1$, $R^2$, $R^3$, $R^4$ and $R^5$, and $R^{1*}$, $R^{2*}$, $R^{3*}$, $R^{4*}$ and $R^{5*}$, and $R^{1}$, $R^{2}$, $R^{3}$, $R^{4}$ and $R^{5**}$ have the abovementioned meanings and A, A* and A** denote an ethylene group or a 2-methylethylene group, and esters thereof and salts thereof, is characterised in that a compound of the general formula II, II* or II*** wherein $R^6$, $R^7$, $R^8$, $R^9$ and $R^{10}$, or $R^{6*}$, $R^{7*}$, $R^{8*}$, $R^{9*}$ and $R^{10*}$, or $R^{6}$, $R^{7}$, $R^{8}$, $R^{9}$ and $R^{10**}$ have the abovementioned meanings is reacted with an acrylic or methacrylic acid derivative of the general formula

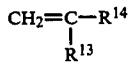

wherein
$R^{13}$ denotes a hydrogen atom or a methyl group and $R^{14}$ denotes a nitrile group or a carboxymethyl or carboxyethyl group,
in the presence of a strong base and, if appropriate, a radical $R^{14}$ which denotes a nitrile group is converted into a carboxyl group and, if appropriate, the radicals $R^9$ and $R^{10}$, if they denote nitro groups, are converted into amino groups or dialkylamino groups, the alkyl radicals having 1 to 4 carbon atoms, and, if desired, the radicals $R^6$, $R^7$ and $R^8$, if they denote nitro groups, are converted into amino groups, which are converted, if desired, into dialkylamino groups, the alkyl radicals having 1 to 4 carbon atoms, and, if desired, the radicals $R^6$, $R^7$, $R^8$, $R^9$ and $R^{10}$, or $R^{6*}$, $R^{7*}$, $R^{8*}$, $R^{9*}$ and $R^{10*}$, or $R^{9}$ and $R^{10}$, if they denote alkoxy grops, are converted into hydroxyl groups, an acid obtained is converted into a salt or an ester with a $C_1$ to $C_5$-alkanol, preferably methanol or ethanol, a salt obtained is converted into the free acid, an ester or another salt, or an ester obtained is converted into the free acid or into a salt or another ester.

The process according to the invention is preferably carried out in non-aqueous organic solvents, such as, for example, dimethylformamide, dimethylsulphoxide, benzene, methylene chloride, chloroform, acetone, ethyl methyl ketone and, in particular, tetrahydrofuran.

By strong bases there are to be understood those with whose use the expert is familiar in the alkylation of nitrogen atoms, such as, for example, alkali metal hydrides, preferably sodium hydride, or alkali metal hydroxides, preferably potassium hydroxide, and alkali metal carbonates, such as sodium carbonate and potassium carbonate.

The reaction with ω-halogenoalkanecarboxylic acids or ω-halogenoalkanecarboxylic acid derivatives is carried out without or with the addition of catalysts. Possible catalysts are those which are customary for this type of reaction, of which tetraalkylammonium salts, such as, for example, tetrabutylammonium chloride, tetradecyltrimethylammonium bromide and tri-($C_8$ to $C_{10}$-alkyl)-methylammonium chloride (tradename: Adogen 464), may be mentioned as examples. The preferred catalyst is tetrabutylammonium bromide.

The reaction temperature can be varied within wide limits, for example from 0° to 100° C., temperatures from 15° to 50° C. being preferred.

The reaction of compounds of the general formulae II, II* or II** with an acrylic or methacrylic acid derivative is carried out under the conditions customary for the addition of amines onto α,β-unsaturated carbonyl compounds. It is not necessary, but expedient, for basic catalysts to be present. Possible basic catalysts are quaternary ammonium hydroxides, such as, for example, benzyltrimethylammonium hydroxide. It is expedient to carry out the reaction in inert solvents, such as benzene, toluene or methylene chloride. However, the reaction is preferably carried out without solvents, an excess of acrylic or methacrylic acid derivative being advantageous. The reaction temperature is from 10° to 100° C. The reaction is preferably carried out at the boiling point of the solvent or of the reaction mixture.

A nitrile group is converted into a carboxyl group within the context of the process according to the invention in the customary manner by saponification with strong acids, such as hydrogen halide acids, in particular hydrochloric acid, or with strong bases, such as alkali metal hydroxides, preferably sodium hydroxide, in aqueous solution or in a mixture of water and solvents such as ethylene glycol. The reaction temperature can be varied within wide limits, for example from room temperature to 120° C.; the reaction is preferably carried out at the boiling point of the reaction mixture.

An alkoxy group is converted into a hydroxyl group in the context of the process according to the invention in a manner which is known per se by saponification with strong acids, such as hydrogen halide acids, preferably hydrobromic acid or hydriodic acid, for example in aqueous solution or in glacial acetic acid, or with suitable Lewis acids, such as, for example boron tribromide, in non-aqueous solvents, such as, for example, methylene chloride. The reaction temperature can be varied within wide limits, for example from room temperature to 100° C.; the reaction is preferably carried out at the boiling point of the reaction mixture, and volatile reaction products, such as alkyl halides, can at the same time be distilled off from the reaction mixture.

A nitro group is converted into an amino group in the context of the process according to the invention in a manner which is known per se by catalytic reduction, for example with molecular hydrogen, if desired under increased pressure, a possible catalyst being, for example, Raney nickel, or with other reducing agents, such as metallic iron, tin or zinc, in strong, non-oxidising acids, such as hydrochloric acid, or with hydrazines in alcohols, water or alcohol/water mixtures, at temperatures of approximately room temperature, for example 15° to 40° C., or at the boiling point of the reaction mixture.

Esterification of a free acid, alkylation of an amine or trans-esterification or saponification of an alkyl ester in the context of the inventive process is carried out in a manner with which the expert is familiar.

The starting materials of the general formulae II, II* and II**, wherein the substituents have the abovementioned meanings, are known, or they can be prepared in a manner which is known per se.

The starting materials required for the preparation of the quinolinones according to the invention which are aryl-substituted in the 3-position can be prepared, for example, by condensation of correspondingly substituted 2-chlorobenzaldehydes and 2-arylmethyl-4,4-dimethyl-2-oxazolines at 170° to 220° C. in high-boiling solvents or solvent mixtures, such as, for example, xylene/N-methylpyrrolidin-2-one, water being separated off, in accordance with the method of H. L. Wehrmeister, J. Heterocycl.Chem. 13, 61 (1976). Another preparation method consists in cyclising α-aryl-2-aminocinnamic acids [M. Pailer, A. Schleppnik, A. Meller, Monatsh.Chem. 96, 1695 (1965); and N. Oda, Yakugaku Zasshi 82, 1115 (1962)]. Other preparation processes are given, for example, by B. M. Bolotin et al, Zh.Vses.Khim.Obshchest. 1972, 460; H. Shirai, N. Oda, Yakugaku Zasshi, 79, 241 (1959); C. E. Kaslow, B.

Buchner, J.Org.Chem. 23, 271 (1958) and D. Johnson, H. Suschnitzky, Tetrahedron Lett. 1974, 4277.

The starting materials required for the preparation of the quinolinones according to the invention which are aryl-substituted in the 4-position can be prepared, for example, by reaction of correspondingly substituted anilines with correspondingly substituted benzoylacetic acid ethyl esters in accordance with the method given by C. R. Hauser, G. A. Reynolds, J.Amer.Chem. Soc. 70, 2402 (1948) and E. F. M. Stephenson, J.Chem.Soc. 1956, 2557. Other methods of preparation are found, for example, in J. Reisch, Angew.Chem. 75, 1203 (1965); B. Staskun, S. S. Israelstam, J.Org.Chem. 26, 3191 (1961); S. C. Bell et al., J.Org.Chem. 27, 562 (1962) and S. Nakano, Yakugaku Zasshi, 82, 492 (1962).

The following examples illustrate the invention in more detail, without restricting it. The abbreviations m. and b.p. denote melting point and boiling point respectively.

EXAMPLES

Example 1

7-Chloro-1,2-dihydro-2-oxo-3-phenylquinol-1-yl-acetic acid ethyl ester 18 g of 7-chloro-1,2-dihydro-2-oxo-3-phenylquinoline, 11.7 g of bromoacetic acid ethyl ester, 2.3 g of tetrabutylammonium bromide and 5.6 g of powdered potassium hydroxide are stirred in 250 ml of tetrahydrofuran at room temperature for 16 hours. The mixture is poured into 1 l of ice-water, acidified to pH 3 to 4 with dilute sulphuric acid and extracted with methylene chloride (2×200 ml) and the organic phase is dried over sodium sulphate and concentrated. The solid brown residue is stirred with 100 ml of cyclohexane, filtered off and recrystallised from ethanol. 10.0 g of the title compound of m. 142°–143° C. are obtained.

EXAMPLE 2

7-Chloro-1,2-dihydro-2-oxo-3-phenylquinol-1-yl-acetic acid 9.5 g of 7-chloro-1,2-dihydro-2-oxo-3-phenylquino-1-yl-acetic acid ethyl ester, 30 ml of 1 N sodium hydroxide solution and 30 ml of ethanol are stirred at 40° C. for 2 hours. 50 ml of 1 N hydrochloric acid and 50 ml of water are added and the precipitate which has separated out is then filtered off. After recrystallisation from ethanol/water with active charcoal, 6 g of the title compound of m. 219°–221° C. are obtained.

EXAMPLE 3

1,2-Dihydro-2-oxo-3-phenylquinol-1-yl-acetic acid ethyl ester 17 g of 1,2-dihydro-2-oxo-3-phenylquinoline, 12.8 g of bromoacetic acid ethyl ester, 2.5 g of tetrabutylammonium bromide and 6.2 g of powdered potassium hydroxide are stirred in 250 ml of tetrahydrofuran at room temperature for 16 hours. The mixture is poured into 1 l of ice-water, acidified to pH 3 to 4 with dilute sulphuric acid and extracted with diethyl ether and the organic phase is dried over sodium sulphate, treated with active charcoal and concentrated. 17.1 g of the title compound are obtained as a viscous, yellow oil.

EXAMPLE 4

1,2-Dihydro-2-oxo-3-phenylquinol-1-yl-acetic acid 8.5 g of the title compound of m. 177°–178° C. (recrystallised from ethanol/cyclohexane) are obtained from 17 g of 1,2-dihydro-2-oxo-3-phenylquinol-1-yl-acetic acid ethyl ester, 56 ml of 1 N sodium hydroxide solution and 56 ml of ethanol by the procedure described in Example 2.

EXAMPLE 5

3-(7-Chloro-1,2-dihydro-2-oxo-3-phenylquinol-1-yl)-propionic acid methyl ester 1 ml of benzyltrimethylammonium hydroxide is added to a suspension of 8 g of 7-chloro-1,2-dihydro-2-oxo-3-phenylquinoline in 21.3 ml of methyl acrylate at 40° to 50° C., under nitrogen, the mixture is stirred at this temperature for 3½ hours and the excess methyl acrylate is then distilled off in vacuo. The solid residue is dissolved in 100 ml of methylene chloride and the solution is washed with 2 N acetic acid, sodium bicarbonate solution and water. After drying the organic phase over sodium sulphate and distilling off the solvent, the residue is recrystallised from cyclohexane. 8.0 g of the title compound of m. 122°–124° C. are obtained.

EXAMPLE 6

3-(7-Chloro-1,2-dihydro-2-oxo-3-phenylquinol-1-yl)-propionic acid 5.6 g of the title compound of m. 196°–199° C. are obtained from 7.0 g of 3-(7chloro-1,2-dihydro-2-oxo-3-phenylquinol-1-yl)-propionic acid methyl ester, 21 ml of 1 N sodium hydroxide solution and 21 ml of methanol by the procedure described in Example 2.

EXAMPLE 7

3-(4-Chlorophenyl)-1,2-dihydro-2-oxoquinol-1-yl-acetic acid ethyl ester 0.98 g of the title compound of m. 101°–103° C. (recrystallised from ethanol/cyclohexane) is obtained from 1.28 g of 3-(4-chlorophenyl)-1,2-dihydro-2-oxoquinoline, 0.85 g of bromoacetic acid ethyl ester, 161 mg of tetrabutylammonium chloride and 400 mg of potassium hydroxide by the procedure described in Example 1, after a reaction period of 2 hours.

EXAMPLE 8

3-(4-Chlorophenyl)-1,2-dihydro-2-oxoquinol-1-yl-acetic acid 4.57 g of the title compound of m. 232°–235° C. are obtained from 6.2 g of 3-(4-chlorophenyl)-1,2-dihydro-2-oxoquinol-1-yl-acetic acid ethyl ester, 20 ml of 1 N sodium hydroxide solution and 20 ml of ethanol by the procedure described in Example 2.

EXAMPLE 9

4-[3-(4-Chlorophenyl)-1,2-dihydro-2-oxoquinol-1-yl]-butyric acid ethyl ester 6.1 g of the title compound of m. 86°–89° C. (recrystallised from ethanol/cyclohexane) are obtained from 10.0 g of 3-(4-chlorophenyl)-1,2-dihydro-2-oxoquinoline, 7.8 g of 4-bromobutyric acid ethyl ester, 1.29 g of tetrabutylammonium bromide and 3.2 g of potassium hydroxide by the procedure described in Example 1, in

EXAMPLE 10

4-[3-(4-Chlorophenyl)-1,2-dihydro-2-oxoquinol-1-yl]-butyric acid 3.77 g of the title compound of m. 205°–207° C. (recrystallised from ethanol) are obtained from 5.5 g of 4-[3-(4-chlorophenyl)-1,2-dihydro-2-oxoquinol-1-yl]-butyric acid ethyl ester, 16 ml of 1 N sodium hydroxide solution and 16 ml of ethanol by the procedure described in Example 2.

EXAMPLE 11

3-(1,2-Dihydro-2-oxo-3-phenylquinol-1-yl)-propionic acid methyl ester

The title compound of m. 77°–80° C. (recrystallised from cyclohexane) is obtained from 1.1 g of 1,2-dihydro-2-oxo-3-phenylquinoline, 10 ml of methyl acrylate and 0.2 ml of benzyltrimethylammonium hydroxide by the procedure described in Example 5.

EXAMPLE 12

4-[1,2-Dihydro-3-(4-methoxyphenyl)-2-oxoquinol-1-yl]-butyric acid ethyl ester 4.5 g of the title compound of m. 101°–105° C. (recrystallised from ethanol/water) are obtained from 7.5 g of 1,2-dihydro-3-(4-methoxyphenyl)-2-oxoquinoline, 5.8 g of 4-bromobutyric acid ethyl ester, 0.96 g of tetrabutylammonium bromide and 2.4 g of potassium hydroxide by the procedure described in Example 1.

EXAMPLE 13

4-[1,2-Dihydro-3-(4-methoxyphenyl)-2-oxoquinol-1-yl]-butyric acid 3.4 g of the title compound of m. 152°–155° C. are obtained from 4.0 g of 4-[1,2-dihydro-3-(4-methoxyphenyl)-2-oxoquinol-1-yl]-butyric acid ethyl ester, 11 ml of 1 N sodium hydroxide solution and 11 ml of ethanol by the procedure described in Example 2.

EXAMPLE 14

4-[7-Chloro-1,2-dihydro-3-(4-methoxyphenyl)-2-oxoquinol-1-yl]-butyric acid ethyl ester 4.2 g of the title compound of m. 84°–88° C. (recrystallised from ethanol/cyclohexane) are obtained from 7.0 g of 7-chloro-1,2-dihydro-3-(4-methoxyphenyl)-2-oxoquinoline, 6.13 g of 4-bromobutyric acid ethyl ester, 1.5 g of tetrabutylammonium bromide and 2.5 g of potassium hydroxide in 150 ml of tetrahydrofuran by the procedure described in Example 1.

EXAMPLE 15

5-(1,2-Dihydro-2-oxo-3-phenylquinol-1-yl)-valeric acid ethyl ester 8.0 g of the title compound are obtained as a viscous yellowish oil from 6.0 g of 1,2-dihydro-2-oxo-3-phenylquinoline, 5.7 g of 5 bromovaleric acid ethyl ester, 0.87 g of tetrabutylammonium bromide and 2.2 g of potassium hydroxide in 150 ml of tetrahydrofuran by the procedure described in Example 1.

EXAMPLE 16

4-[7-Chloro-1,2-dihydro-3-(4-methoxyphenyl)-2-oxoquinol-1-yl]butyric acid 2.6 g of the title compound of m. 175°–177° C. (recrystallised from ethanol) are obtained from 4.0 g of 4-[7-chloro-1,2-dihydro-3-(4-methoxyphenyl)-2-oxoquinol-1-yl]-butyric acid ethyl ester, 12 ml of 1 N sodium hydroxide solution and 12 ml of water by the procedure described in Example 2.

EXAMPLE 17

7-Chloro-3-(4-chlorophenyl)-1,2-dihydro-2-oxoquinoline 17.5 g of 2,4-dichlorobenzaldehyde, 22.4 g of 2-(4-chlorobenzyl)-4,4-dimethyl-2-oxazoline, 1 g of sodium bisulphate, 50 ml of 1-methyl-2-pyrrolidinone and 30 ml of xylene are heated at a bath temperature of 170° to 220° C., using a water separator, until 3.2 ml of water and 20 ml of xylene have been separated off. After cooling the reaction mixture, methanol is added and the title compound (m.>300° C.) is collected by filtration (yield: 24.8 g).

EXAMPLE 18

7-Chloro-3-(4-chlorophenyl)-1,2-dihydro-2-oxoquinol-1-yl-acetic acid ethyl ester 1.3 g of the title compound are obtained as a viscous yellowish oil from 1.45 g of 7-chloro-3-(4-chlorophenyl)-1,2-dihydro-2-oxoquinoline, 0.83 g of bromoacetic acid ethyl ester, 160 mg of tetrabutylammonium bromide and 400 mg of potassium hydroxide by the procedure described in Example 1.

EXAMPLE 19

1,2-Dihydro-2-oxo-4-phenylquinol-1-yl-acetic acid ethyl ester

The title compound is obtained as a light-brown oil from 6.6 g of 1,2-dihydro-2-oxo-4-phenylquinoline, 5.0 g of bromoacetic acid ethyl ester, 1.0 g of tetrabutylammonium bromide and 2.5 g of potassium hydroxide in 200 ml of tetrahydrofuran by the procedure described in Example 1.

EXAMPLE 20

1,2-Dihydro-2-oxo-4-phenylquinol-1-yl-acetic acid

The title compound of m. 218°–221° C. (recrystallised from ethyl acetate) is obtained from 1,2-dihydro-2-oxo-4-phenylquinol-1-yl-acetic acid ethyl ester (obtained according to Example 19), 1 N sodium hydroxide solution and ethanol by the procedure described in Example 2.

EXAMPLE 21

4-(1,2-Dihydro-2-oxo-4-phenylquinol-1-yl)-butyric acid ethyl ester (a) 3.0 g of 1,2-dihydro-2-oxo-4-phenylquinoline, 3.97 g of 4-bromobutyric acid ethyl ester and 2.8 g of potassium carbonate in 75 ml of ethyl methyl ketone are boiled under reflux for 36 hours. The reaction mixture is poured into 150 ml of water and extracted with 2×150 ml of diethyl ether and the organic phase is dried over sodium sulphate and concentrated. The oily residue is a mixture of the title compound and 4-(4-phenylquinol-2-yl)-oxybutyric acid ethyl ester, which is separated into the components by column chromatography (silica gel, eluting agent: chloroform). The product with the smaller $R_f$ value is the oily title compound.

(b) The oily title compound is obtained from 6.6 g of 1,2-dihydro-2-oxo-4-phenylquinoline, 5.8 1 g of 4-bromobutyric acid ethyl ester, 1.0 g of tetrabutylammonium bromide and 2.5 g of potassium hydroxide in 200 ml of tetrahydrofuran by the procedure described in Example b 1.

EXAMPLE 22

4-(1,2-Dihydro-2-oxo-4-phenylquinol-1-yl)-butyric acid 6.35 g of the title compound of m. 215°–216° C. are obtained from the 4-(1,2-dihydro-2-oxo-4-phenylquinol-1-yl)-butyric acid ethyl ester obtained according to Example 21b), 60 ml of ethanol and 60 ml of 1 N sodium hydroxide solution by the procedure described in Example 2.

EXAMPLE 23

3-(1,2-Dihydro-2-oxo-4-phenylquinol-1-yl)-propionitrile 6.9 g of 1,2-dihydro-2-oxo-4-phenylquinoline are suspended in 45 ml of acrylonitrile, and 3 ml of benzyltrimethylammonium hydroxide are added at 40° to 45° C. During this addition, the mixture starts to boil. After boiling for ten minutes, the acrylonitrile is largely distilled off in vacuo. The residue is heated with 300 ml of ethanol to the boiling point, undissolved material is filtered off and the filtrate is treated with active charcoal and concentrated to 200 ml. The mixture is left to stand for 12 hours and the title compound which has separated out (6.4 g of m. 162°–165° C.) is filtered off.

EXAMPLE 24

3-(1,2-Dihydro-2-oxo-4-phenylquinol-1-yl)-propionic acid 7.1 g of 3-(1,2-dihydro-2-oxo-4-phenylquinol-1-yl)-propionitrile and 100 ml of concentrated hydrochloric acid are boiled under reflux for 3 hours. The mixture is allowed to cool and the precipitate is filtered off and recrystallised from ethyl acetate. 6.0 g of the title compound of m. 147°–148° C. are obtained.

EXAMPLE 25

6-(1,2-Dihydro-2-oxo-4-phenylquinol-1-yl)-hexanoic acid ethyl ester 13.0 g of the semi-crystalline title compound are obtained from 7.3 g of 1,2-dihydro-2-oxo-4-phenylquinoline, 8.5 g of 6-bromohexanoic acid ethyl ester, 1.3 g of tetrabutylammonium bromide and 3.5 g of potassium hydroxide in 250 ml of tetrahydrofuran by the procedure described in Example 1.

EXAMPLE 26

6-(1,2-Dihydro-2-oxo-4-phenylquinol-1-yl)-hexanoic acid 3.3 g of the title compound of m. 157°–158° C. (recrystallised from ethanol) are obtained from 13.0 g of 6-(1,2-dihydro-2-oxo-4-phenylquinol-1-yl)-hexanoic acid ethyl ester, 60 ml of 1 N sodium hydroxide solution and 60 ml of ethanol by the procedure described in Example 2.

EXAMPLE 27

7-Chloro-1,2-dihydro-2-oxo-3-phenylquinoline 17.5 g of 2,4-dichlorobenzaldehyde, 18.9 g of 2-benzyl-4,4-dimethyl-2-oxazoline, 1 g of sodium bisulphate, 50 ml of 1-methylpyrrolidin-2-one and 30 ml of xylene are heated at a bath temperature of 170° C., using a water separator, until 2 ml of water have been separated off. 20 ml of solvent are then distilled off at a bath temperature of 220° C., the mixture is stirred under reflux at this temperature for a further 15 minutes and, after cooling, 300 ml of water are added. The precipitate which has separated out is filtered off and washed with water and methanol. Yield: 21.26 g of m. 254°–258° C.

EXAMPLE 28

3-(4-Chlorophenyl)-1,2-dihydro-2-oxo-quinoline 14.35 g of the title compound of m. 260°–262° C. are obtained from 16.0 g of 2-chlorobenzaldehyde, 22.4 g of 2-(4-chlorobenzyl)-4,4-dimethyl-2-oxazoline, 1 g of sodium bisulphate, 50 ml of 1-methylpyrrolidin-2-one and 30 ml of xylene by the procedure described in Example 27.

EXAMPLE 29

Ampoules containing 1,800 mg of 7-chloro-1,2-dihydro-2-oxo-3-phenylquinol-1-yl-acetic acid, 250 kg batch size 25 kg of 1,2-propylene glycol and 150 kg of doubly distilled water are taken, 15 kg of 7-chloro-1,2-dihydro-2-oxo-3-phenylquinol-1-yl-acetic acid are added and 14.5 kg of sodium hydroxide solution (10% strength by weight NaOH) are then slowly added, whilst stirring. When all the solids have dissolved, the pH is adjusted to 7.5–8.0 with dilute hydrochloric acid. 0.0625 kg of sodium pyrosulphite are added and the mixture is stirred until all the solids have dissolved. The solution is made up to 250 kg with doubly distilled water. It is filled into 30 ml ampoules and sterilised in an autoclave at 120° C. for 30 minutes.

EXAMPLE 30

Ampoules containing 1,200 mg of 4-[3-(4-chlorophenyl)-1,2-dihydro-2-oxo-quinol-1-yl]-butyric acid, 250 kg batch size 50 kg of 1,2-propylene glycol and 150 kg of doubly distilled water are taken. 15 kg of 4-[3-(4-chlorophenyl)-1,2-dihydro-2-oxoquinol-1-yl]-butyric acid are then added, whilst stirring. 13.4 kg of 10% strength sodium hydroxide solution are subsequently added, and the pH of the solution is then adjusted to 8.0 with dilute hydrochloric acid. The solution is made up to 250 kg with doubly distilled water. It is filled into 20 ml ampoules and sterilised in an autoclave at 120° C. for 30 minutes.

EXAMPLE 31

Tablets containing 50 mg of 3-(1,2-dihydro-2-oxo-4-phenyl-quinol-1-yl)-propionic acid 25 kg of 3-(1,2-dihydro-2-oxo-4-phenyl-quinol-1-yl)-propionic acid, 25 kg of xylitol and 26 kg of calcium phosphate are granulated with 2.5 kg of polyvinylpyrrolidone (MW—25,000; MW=molecular weight) in approximately 6 l of water. The granules are pressed through a sieve of 1.25 mm mesh width and, after drying, 8 kg of carboxymethylcellulose, 2.5 kg of talc and 1 kg of magnesium stearate are added. The dry granules are pressed to tablets which are 8 mm in diameter, weigh 250 mg and have a hardness of 5–6 kg.

EXAMPLE 32

Tablets containing 100 mg of 3-(7-chloro-1,2-dihydro-2-oxo-3-phenyl-quinol-1-yl)-propionic acid 40 kg of 3-(7-chloro-1,2-dihydro-2-oxo-3-phenyl-quinol-1-yl)-propionic acid, 25 kg of xylitol and 16 kg of calcium phosphate are granulated with 4 kg of polyvinylpyrrolidone (MW—25,000) in approximately 5.5 l of water and the granules are pressed through a sieve of 1.25 mm mesh width. After drying, 10 kg of carboxymethylcellulose, 4 kg of talc and 2 kg of magnesium stearate are added. The granules are pressed, on a cam-type machine, to tablets which are 9 mm in diameter, weigh 250 mg and have a hardness of 4–5 kg.

EXAMPLE 33

Tablets containing 300 mg of 4-[1,2-dihydro-3-(4-methoxyphenyl)-2-oxo-quinol-1-yl]-butyric acid 60 kg of 4-[1,2-dihydro-3-(4-methoxyphenyl)-2-oxo-quinol-1-yl]-butyric acid, 12 kg of xylitol and 8 kg of calcium phosphate are granulated with 5 kg of polyvinylpyrrolidone (MW—25,000) in approximately 6 l of water and the granules are pressed through a sieve of 1.25 mm mesh width. After drying, 10 kg of carboxymethylcellulose, 4 kg of talc and 2 kg of magnesium stearate are added. The granules are pressed, on a rotary machine, to tablets which are 11 mm in diameter, weigh 500 mg and have a hardness of 6–7 kg.

EXAMPLE 34

25,000 tablets with an active compound content of 1,800 mg of 7-chloro-1,2-dihydro-3-phenyl-2-oxo-quinol-1-yl-acetic acid 40 kg of 7-chloro-1,2-dihydro-3-phenyl-2-oxoquinol-1-yl-acetic acid, 13 kg of maize starch, 0.6 kg of amorphous silica and 0.8 kg of sodium lauryl sulphate are granulated with 1 kg of polyvinylpyrrolidone in 6 l of ethanol and the granules are pressed through a sieve of 1.25 mm mesh width. After drying at 40° C., 3.2 kg of pectin, 1.0 kg of talc and 0.4 kg of magnesium stearate are added. The granules are pressed, on a rotary machine, to tablets which are 17 mm in diameter, weigh 2.4 g and have a hardness of 10–12 kg.

EXAMPLE 35

10,000 capsules with an active compound content of 50 mg of 1,2-dihydro-2-oxo-3-phenyl-quinol-1-yl-acetic acid 500 g of 1,2-dihydro-2-oxo-3-phenyl-quinol-1-yl-acetic acid, 495 g of micro-crystalline cellulose and 5 g of amorphous silica are mixed thoroughly and the mixture is filled into size 4 hard gelatin capsules.

EXAMPLE 36

10,000 capsules with an active compound content of 800 mg of 4-[3-(4-chlorophenyl)-1,2-dihydro-2-oxo-quinol-1-yl]-butyric acid 8 kg of 4-[3-(4-chlorophenyl)-1,2-dihydro-2-oxo-quinol-1-yl]-butyric acid are mixed thoroughly with 900 g of micro-crystalline cellulose and 100 g of amorphous silica and the mixture is filled into size 000 hard gelatin capsules.

PHARMACOLOGY

The quinolinone-alkanecarboxylic acids according to the invention and their esters and salts increase glucose synthesis in the liver and thus the level of glucose in the blood.

In the table which follows, the compounds investigated are characterised by serial numbers, these being allocated as follows:

| Serial No. | Name of the compound |
|---|---|
| 1 | 7-Chloro-1,2-dihydro-2-oxo-3-phenyl-quinol-1-yl-acetic acid |
| 2 | 1,2-Dihydro-2-oxo-3-phenyl-quinol-1-yl-acetic acid |
| 3 | 3-(7-Chloro-1,2-dihydro-2-oxo-3-phenyl-quinol-1-yl)-propionic acid |
| 4 | 3-(1,2-Dihydro-2-oxo-4-phenyl-quinol-1-yl)-propionic acid |
| 5 | 4-[3-(4-Chlorophenyl)-1,2-dihydro-2-oxo-quinol-1-yl]-butyric acid |
| 6 | 4-[1,2-Dihydro-3-(4-methoxyphenyl)-2-oxo-quinol-1-yl]-butyric acid |
| 7 | 6-(1,2-Dihydro-2-oxo-4-phenyl-quinol-1-yl)-caproic acid |

Investigations into the influence of representatives of the compounds according to the invention on the formation of glucose in rat livers perfused in isolation are shown in Table I. The maximum increase in the formation of glucose in the liver from lactate/pyruvate which can be achieved by adding 0.100 mmol/l of substance to the perfusion medium of the rat livers perfused in isolation is given.

TABLE I

| Serial No. | Glucose formation (liver, in vitro) increase (in %) Concentration: 0.100 mmol/l |
|---|---|
| 1 | 190 |
| 2 | 121 |
| 3 | 49 |
| 4 | 61 |
| 5 | 151 |
| 6 | 128 |
| 7 | 33 |

The influence of the compounds according to the invention on the formation of glucose was determined by the following method:

Sprague-Dawley rats (body weight: 160–200 g) are used. The animals are kept in Makrolon cages with up to 5 animals per cage (room temperature: 23° C., relative atmospheric humidity: 55%, fixed day/night rhythm (12/12 hours), standard rat diet of Altromin ®). The feed is withdrawn from the animals 20 to 22 hours before the operation. Water is taken in ad libitum. The removal and perfusion of the liver are carried out in accordance with the technique devised by R. Scholz et al., [Eur.J.Biochem. 38 (1973) 64–72]. Krebs-Henseleit bicarbonate buffer (pH 7.4) which is saturated with an oxygen/carbon dioxide mixture (95/5) and contains 1.6 mmols/l of L-lactate and 0.2 mmol/l of pyruvate is used as the perfusion liquid. The perfusion liquid is pumped into the liver via a cannula inserted in the portal vein. The perfusion liquid leaving the liver is collected via a cannula inserted in the vena cava and then passed over an oxygen electrode. The liver is perfused for 2 hours. The test compounds are infused in an increasing concentration (0.01, 0.03 and 0.10 mmol/l) from the 32nd to 80th minute of the perfusion.

Samples of the perfusion liquid leaving the liver are collected at one minute intervals and are analysed for glucose, lactate and pyruvate by standard enzymatic methods. The oxygen content is determined continuously by means of a platinum electrode. The percentage values given in Table I relate to the state existing before and after addition of the compounds, the glucose formation resulting solely from lactate and pyruvate being set at 100%.

7-Chloro-1,2-dihydro-2-oxo-3-phenylquinol-1-yl-acetic acid and its salts with inorganic and organic bases, a process for their preparation as described in Examples 1 and 2, and medicaments and feed additives containing it or its salts are preferred embodiments of the invention.

We claim:

1. A substituted quinolinone of the general formula I

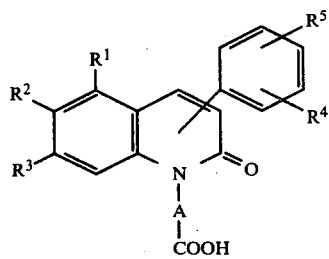

wherein
$R^1$, $R^2$ and $R^3$ are identical or different and each denotes a hydrogen atom, a halogen atom, a hydroxyl group, an alkoxy group with 1 to 4 carbon atoms, an amino group, a dialkylamino group, each alkyl radical having 1 to 4 carbon atoms, or a nitro group,
$R^4$ and $R^5$ are identical or different and each denotes a hydrogen atom, a halogen atom, an alkoxy group with 1 to 4 carbon atoms, a hydroxyl group, an amino group or a dialkylamino group, each alkyl radical having 1 to 4 carbon atoms, or
$R^4$ and $R^5$ together denote a methylenedioxy group bonded to two adjacent ring carbon atoms, and A denotes an alkylene group with 1 to 5 carbon atoms,
an ester thereof with an alkanol with 1 to 5 carbon atoms, or a salt thereof with an inorganic and organic base.

2. A substituted quinolinone of the general formula I*

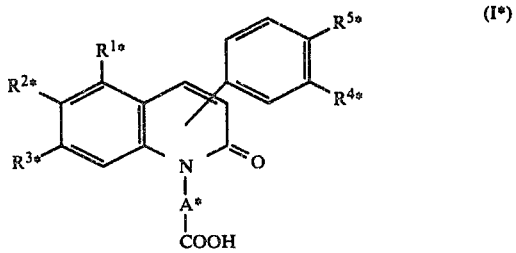

wherein
$R^{1*}$, $R^{2*}$ and $R^{3*}$ are identical or different and each denotes a hydrogen atom, a halogen atom, an alkoxy group with 1 to 4 carbon atoms or a hydroxyl group,
$R^{4*}$ and $R^{5*}$ are identical or different and each denotes a hydrogen atom, a halogen atom, an alkoxy group with 1 to 4 carbon atoms or a hydroxyl group, or
$R^{4*}$ and $R^{5*}$ together denote a methylenedioxy group, and
$A^*$ denotes an alkylene group with 1 to 5 carbon atoms,
an ester thereof with an alkanol with 1 to 5 carbon atoms, or a salt thereof with an organic or organic base.

3. A substituted quinolinone of the general formula I**

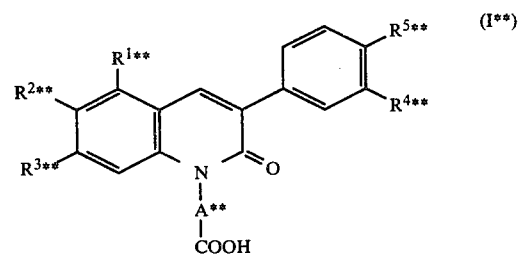

wherein
$R^{1}$ and $R^{2}$ denote a hydrogen atom,
$R^{3**}$ denotes a hydrogen atom or a chlorine atom,
$R^{4}$ and $R^{5}$ are identical or different and each denotes a hydrogen atom, a chlorine atom or a methoxy group and
$A^{**}$ denotes a methylene, ethylene, n-propylene or n-butylene group,
a methyl or ethyl ester thereof and or a salt thereof with an inorganic or organic base.

4. 7-Chloro-1,2-dihydro-2-oxo-3-phenyl-quinol-1-yl-acetic acid or a salt thereof with inorganic and organic base.

5. A pharmaceutical composition containing from 1% to 95% by weight of the total mixture of at least one compound according to claim 1, 2, 3 or 4 in admixture with one or more solid or liquid pharmaceutically acceptable inert carriers.

6. A feed additive containing from 0.1% to 50% by weight of the total mixture of at least one compound according to claim 1, 2, 3 or 4 in admixture with one or more solid or liquid nutritionally acceptable inert carriers.

7. A hyperglycaemic pharmaceutical composition having pharmaceutically-acceptable inert carrier in admixture with an effective amount of a pharmaceutically-acceptable compound according to claim 1, 2, 3 or 4.

8. A compound according to claim 1, 2, 3 or 4 which is an acid, an ester or a pharmacologically-acceptable salt.

* * * * *